US008421486B2

United States Patent
Akiyama et al.

(10) Patent No.: US 8,421,486 B2
(45) Date of Patent: Apr. 16, 2013

(54) OIL-DEGRADATION DETECTING APPARATUS

(75) Inventors: Yo Akiyama, Nagasaki (JP); Akihiko Yano, Nagasaki (JP); Junichi Kaga, Sagamihara (JP); Yoshihiro Deguchi, Yokohama (JP); Taketoshi Yamaura, Nagasaki (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 591 days.

(21) Appl. No.: 12/522,529

(22) PCT Filed: Jun. 18, 2008

(86) PCT No.: PCT/JP2008/061144
§ 371 (c)(1),
(2), (4) Date: Jul. 8, 2009

(87) PCT Pub. No.: WO2008/156112
PCT Pub. Date: Dec. 24, 2008

(65) Prior Publication Data
US 2009/0315574 A1    Dec. 24, 2009

(30) Foreign Application Priority Data
Jun. 19, 2007  (JP) ................. 2007-161651

(51) Int. Cl.
*G01R 27/08* (2006.01)
*G01R 27/26* (2006.01)
*G01N 11/00* (2006.01)

(52) U.S. Cl.
USPC .......... 324/698; 324/689; 324/694; 73/54.01; 73/53.01

(58) Field of Classification Search ............... 324/698, 324/693, 691, 649, 600, 522, 713, 658, 689, 324/694, 663, 664; 702/1, 52, 57, 64, 65, 702/81, 100; 73/53.01, 53.05, 54.01, 61.41, 73/61.42, 61.43, 61.44, 73
See application file for complete search history.

(56) References Cited

U.S. PATENT DOCUMENTS 4,646,070 A    2/1987 Yasuhara et al.
4,733,556 A *  3/1988 Meitzler et al. ............. 73/53.05
(Continued)

FOREIGN PATENT DOCUMENTS

JP    58-85314 A    5/1983
JP    10-78402 A    3/1998
(Continued)

OTHER PUBLICATIONS

Takae et al., "The proposal of new sensing technique for judging the deterioration of engine oil", Dai 18 Kai Proceedings of Sensing Forum-Sensing Gijutsu no Aratana Tenkai to Yugo, 2001, vol. 18, pp. 241-245.

(Continued)

*Primary Examiner* — Hoai-An D Nguyen
(74) *Attorney, Agent, or Firm* — Birch, Stewart, Kolasch & Birch, LLP

(57) ABSTRACT

An oil-degradation detecting apparatus that can more accurately judge oil degradation and a mechanical system having a rotating part or a sliding part and including the oil-degradation detecting apparatus are provided. Two plates (21, 22) are disposed in an oil flow path (11) so as to be parallel to each other, an ammeter (24) measures a current that flows when an AC voltage is applied between the two plates (21, 22), a voltmeter measures the voltage between the plates (21, 22), and a signal processor (processor) (31) determines the electrical conductivity and the dielectric constant of the oil (10) based on the measurement results from the ammeter (24) and the voltmeter (25) and judges degradation of the oil (10) based on the electrical conductivity and the dielectric constant.

7 Claims, 5 Drawing Sheets

U.S. PATENT DOCUMENTS

| | | | |
|---|---|---|---|
| 5,200,027 A * | 4/1993 | Lee et al. | 216/51 |
| 5,274,335 A * | 12/1993 | Wang et al. | 324/689 |
| 5,540,086 A * | 7/1996 | Park et al. | 73/53.05 |
| 5,604,441 A | 2/1997 | Freese et al. | |
| 6,456,873 B1 * | 9/2002 | Inoue et al. | 600/547 |
| 7,504,836 B2 * | 3/2009 | Chambon et al. | 324/698 |
| 7,729,870 B2 * | 6/2010 | Sun | 702/52 |
| 2003/0020494 A1 | 1/2003 | Desmier et al. | |
| 2003/0222656 A1 * | 12/2003 | Phillips et al. | 324/605 |
| 2004/0250606 A1 | 12/2004 | Buttgenbach et al. | |
| 2006/0207315 A1 | 9/2006 | Niemann et al. | |
| 2009/0063060 A1 * | 3/2009 | Sun | 702/52 |
| 2009/0309619 A1 * | 12/2009 | Behle et al. | 324/698 |

FOREIGN PATENT DOCUMENTS

| | | |
|---|---|---|
| JP | 2003-114207 A | 4/2003 |
| JP | 2004-526170 A | 8/2004 |
| JP | 2005-10087 A | 1/2005 |
| JP | 2005-507497 A | 3/2005 |
| JP | 2005-337096 A | 12/2005 |
| JP | 2006-97496 A | 4/2006 |
| JP | 2006-194905 A | 7/2006 |
| JP | 2006-258814 A | 9/2006 |

OTHER PUBLICATIONS

Hagura et al., "Measurement of Deterioration of Frying Oil Using Electrical Properties", Journal of the Japanese Society for Food Science and Technology, Sep. 2006, vol. 53, No. 9, pp. 474-480.

* cited by examiner

OIL-DEGRADATION DETECTING APPARATUS

TECHNICAL FIELD

The present invention relates to an oil-degradation detecting apparatus.

BACKGROUND ART

In general, a mechanical system having a rotating part and a sliding part includes an oil tank or an oil-supplying path for circulating and supplying oil to various components constituting the rotating or sliding part of the mechanical system or peripheral components thereof, and thereby smoothly operates each component while preventing them from becoming worn.

The quality control of the oil in such a mechanical system is conventionally performed by chemical analysis, but chemical analysis takes a long time after oil sampling to give a result. Therefore, quality control cannot be done in a timely manner. Accordingly, there is a demand for developing an apparatus for detecting the state of oil degradation, and some have been proposed.

For example, in the "engine-oil degradation detecting apparatus" disclosed in Japanese Unexamined Patent Application, Publication No. Hei 10-78402, a method has been proposed in which the oil pan of an engine is provided with a resistance sensor for measuring the electrical resistance of the oil, and the driver is informed of the need for an oil change when the measured electrical resistance value of the oil is decreased to a degradation resistance value that is set in advance.

Patent Document 1: Japanese Unexamined Patent Application, Publication No. Hei 10-78402

DISCLOSURE OF INVENTION

However, in the method disclosed in the above-described Patent Document 1, the degradation of oil is judged based on a change in the electrical resistance value, and therefore there are situations where the method is too sensitive to intrusion of materials that highly affect the electrical resistance value, such as intrusion of carbon (soot).

As a measurement method for detecting a degradation state of oil, in addition to methods where a change in the electrical resistance value (electrical conductivity) is measured, as in Patent Document 1, there are known methods to measure a change in viscosity, dielectric constant, optical transmittance, or pH associated with degradation of oil. These methods all have advantages and disadvantages, and there are situations where there is a limit to accurate judgment of oil degradation by measuring a single piece of information.

The present invention has been accomplished for solving the above-mentioned problems, and it is an object thereof to provide an oil-degradation detecting apparatus that can more accurately judge degradation of oil and a mechanical system having a rotating part or a sliding part and including the oil-degradation detecting apparatus.

The present invention employs the following solutions for solving the above-mentioned problems.

A first aspect of the present invention relates to an oil-degradation detecting apparatus including two plates disposed so as to be parallel to each other in a path in which oil flows, an ammeter measuring the current that flows when an AC voltage is applied between the two plates, a voltmeter measuring the voltage between the plates when the AC voltage is applied to the two plates, and a processor determining the electrical conductivity and the dielectric constant of the oil based on measurement results from the ammeter and the voltmeter and judging degradation of the oil based on the electrical conductivity and the dielectric constant.

In the above-mentioned oil-degradation detecting apparatus, the ammeter measures a current, the voltmeter measures a voltage, and the processor may determine a complex impedance between the two plates based on the measurement results from the ammeter and the voltmeter, the electrical conductivity of the oil by assuming the real part of the reciprocal of the complex impedance as a resistance component between the two plates, and the dielectric constant of the oil by assuming the imaginary part of the reciprocal of the complex impedance as a capacitance component between the two plates.

In the first aspect of the present invention, since the degradation of the oil is judged based on the electrical conductivity and the dielectric constant, electrical characteristics associated with degradation of the oil or intrusion of a contaminant can be ascertained two-dimensionally from the viewpoints of the electrical conductivity and the dielectric constant, and thereby oil degradation can be more accurately judged.

In the above-mentioned oil-degradation detecting apparatus, the processor may store the respective acceptable ranges of the electrical conductivity of the oil and the dielectric constant of the oil and judge the oil to be degraded when either the electrical conductivity of the oil or the dielectric constant of the oil is outside the acceptable range thereof.

In the above-mentioned oil-degradation detecting apparatus, the processor may store a table that relates the electrical conductivity of the oil and the dielectric constant of the oil with causes of oil degradation and may identify the cause of the oil degradation by referring to this table.

By doing so, it becomes possible not only to judge the oil degradation but also to identify the cause of the oil degradation.

In the above-mentioned oil-degradation detecting apparatus, the measurement may be performed while varying the frequency of the AC voltage applied to the two plates.

The sensitivities of the electrical conductivity and the dielectric constant can be controlled by making the frequency of the AC voltage variable, and thereby oil degradation can be judged with higher precision.

In the above-mentioned oil-degradation detecting apparatus, the waveform of the AC voltage applied to the two plates is, for example, a sine wave, a square wave, a triangle wave, a sawtooth wave, or a reverse sawtooth wave.

For example, by using a square wave, a triangle wave, a sawtooth wave, or a reverse sawtooth wave as the AC voltage waveform and determining the electrical conductivity and the dielectric constant for a harmonic component, electrical conductivities and dielectric constants for a plurality of frequencies can be obtained simultaneously and the sensitivities of the electrical conductivity and the dielectric constant can be controlled by a single measurement, and thereby oil degradation can be judged with higher precision.

The above-mentioned oil-degradation detecting apparatus may further include a viscometer disposed in the oil flow path and measuring the viscosity of the oil, and the processor may judge degradation of the oil by additionally using the measurement result from the viscometer.

By adding the viscosity to the judgment parameters of the degradation judgment of the oil, it becomes possible to compensate for a decrease in the viscosity due to, for example, intrusion of fuel, and the degradation of the oil can be judged multidimensionally based on the electrical characteristics and the viscosity. Therefore, the degradation judgment can be performed with higher precision and accuracy.

The above-mentioned oil-degradation detecting apparatus may further includes a moisture meter provided in the oil flow path and measuring the moisture of the oil, and the processor may judge the degradation of the oil by additionally using the measurement result from the moisture meter.

By adding the moisture to the judgment parameters of the degradation judgment of the oil, it becomes possible to identify the cause of the change in the electrical characteristics, and the degradation of the oil can be judged multidimensionally based on the electrical characteristics and the moisture. Therefore, the degradation judgment can be performed with higher precision and accuracy.

The above-mentioned oil-degradation detecting apparatus may further include an informing unit reporting the result of the judgment of degradation of the oil by the processor.

The above-mentioned oil-degradation detecting apparatus may further include a partial changing unit that replaces part of the oil with oil of good quality when the processor judges the oil to be degraded.

According to the first aspect of the present invention, the time to maintenance of the system to which the oil-degradation detecting apparatus is applied can be extended. In addition, it is possible to prevent a worst case scenario, such as breakage of the system due to delayed maintenance.

A second aspect of the present invention relates to a mechanical system having a rotating part or a sliding part and including the above-mentioned oil-degradation detecting apparatus.

By having such a configuration, real-time sensing of oil degradation is possible without shutting down of the mechanical system. Furthermore, it is possible to determine the appropriate time for oil change, and thereby an advantage is afforded in that unnecessary oil change work can be avoided.

According to the present invention, since the degradation of oil can be judged based on the electrical conductivity and the dielectric constant, electrical characteristics associated with degradation of the oil or intrusion of a contaminant can be ascertained two-dimensionally from the viewpoints of the electrical conductivity and the dielectric constant. Therefore, an advantage is afforded in that the degradation of the oil can be more adequately judged.

EXPLANATION OF REFERENCE SIGNS

Figure 1:
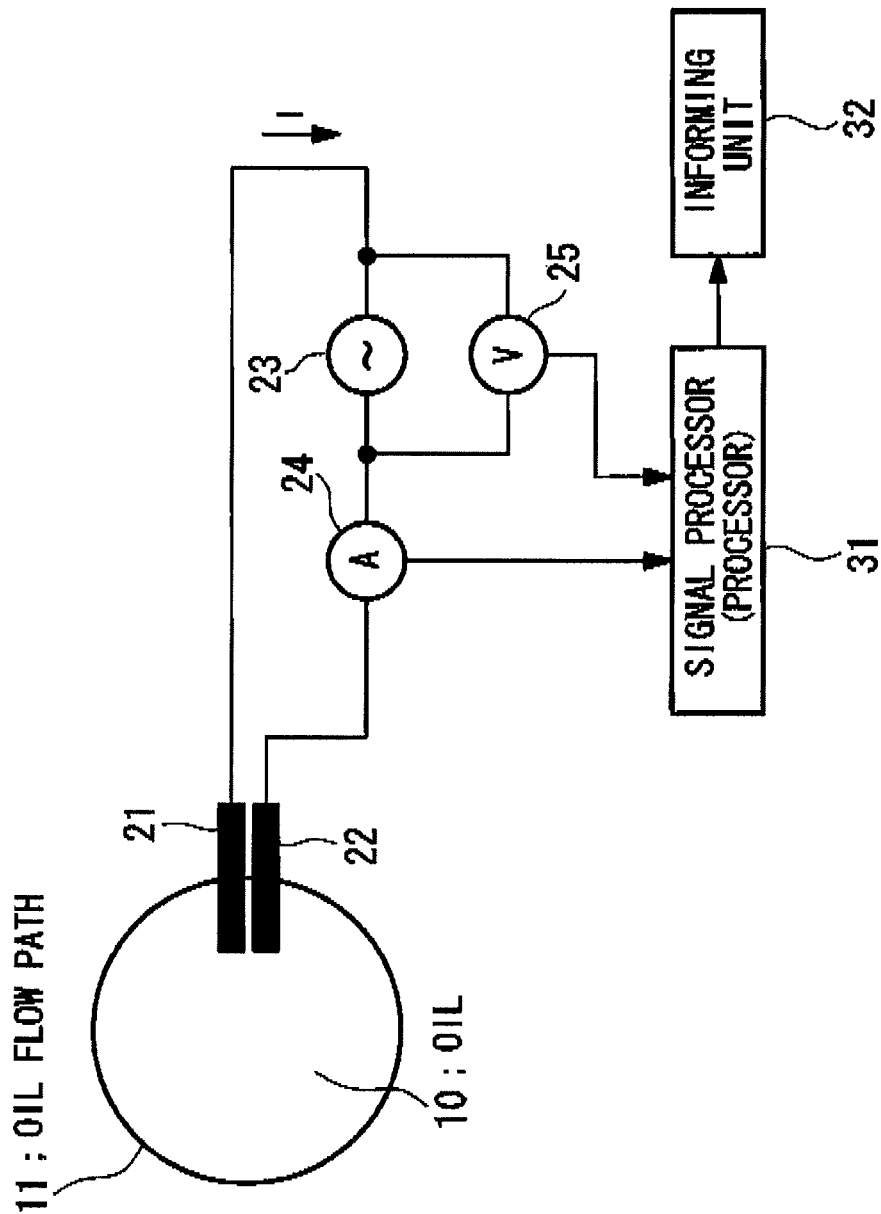
FIG. 1 is a configuration diagram of an oil-degradation detecting apparatus according to an Embodiment of the present invention.

10, 20: oil
11: oil flow path
21, 22: plate
23: AC source
24: ammeter
25: voltmeter
31: signal processor (processor)
32: informing unit
41: effective value comparing unit
42: phase difference calculator
43: resistance value calculator
44: capacitance value calculator
45: electrical conductivity calculator
46: dielectric constant calculator
47: degradation judging unit

BEST MODE FOR CARRYING OUT THE INVENTION

Embodiments of the oil-degradation detecting apparatus according to the present invention will now be described with reference to the drawings.

FIG. 1 is a schematic configuration diagram of an oil-degradation detecting apparatus according to an Embodiment of the present invention.

In the drawing, the oil-degradation detecting apparatus of this Embodiment detects degradation of oil 10 flowing in an oil flow path 11 and is constructed of two plates 21 and 22 disposed in the oil flow path 11 so as to be parallel to each other, an AC source 23 applying an AC voltage between the two plates 21 and 22, an ammeter 24 measuring the current that flows when the AC voltage is applied, a voltmeter 25 measuring the voltage between the plates 21 and 22 when the AC voltage is applied, a signal processor (which corresponds to the processor in the Claims) 31 calculating the electrical conductivity and the dielectric constant of the oil 10 based on the measurement results from the ammeter 24 and the voltmeter 25 and judging degradation of the oil 10 based on the electrical conductivity and the dielectric constant, and an informing unit 32 reporting the results of the judgment of degradation of the oil 10 by the signal processor 31.

As the AC source 23, one that outputs a sine-wave AC voltage which can set the frequency variably is used. The ammeter 24 and the voltmeter 25 that are used are configured, for example, so as to be able to output instantaneous values of the current and voltage, respectively.

The signal processor 31 is embodied by, for example, an MPU (microprocessor), a DSP (digital signal processor), or a PC and calculates the electrical conductivity and the dielectric constant. The process for judging degradation of the oil 10 is achieved programmatically. The PC or the like may be configured such that it can also serve as a controller that controls the entirety or part of an apparatus to which the oil-degradation detecting apparatus is applied, such as an internal-combustion engine. When a plurality of pairs of plates 21 and 22 are provided in the oil flow path 11, the signal processor 31 may be provided for each pair of plates 21 and 22, or one single signal processor 31 may collectively process the plurality of pairs of plates 21 and 22.

The informing unit may be of any form that reports the result of degradation judgment, and various configurations are possible; for example, when the oil 10 is judged to be degraded, an alarm (warning sound) is outputted, a predetermined position on a display panel blinks, or a message showing that the oil 10 is degraded is displayed.

Figure 2A:
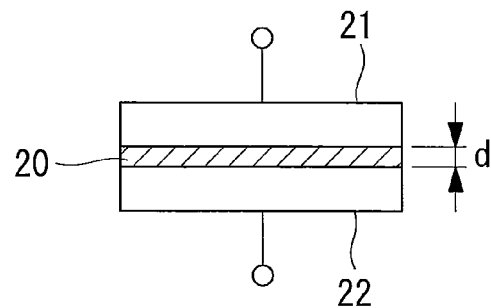
FIG. 2A is a cross-sectional view of plates 21 and 22 and an oil 20 lying between the plates.

Furthermore, as shown in FIG. 2A, the two plates 21 and 22 are flat plates parallel to each other with a distance d therebetween and having the same planar shape with a predetermined planar area S and are disposed in the oil flow path 11. When an oil filter is disposed in the oil flow path 11, the two plates 21 and 22 are desirably disposed after the oil filter (downstream in the flow of the oil 10).

Next, the measurement principle of the oil-degradation detecting apparatus according to this Embodiment will be described.

Figure 2B:
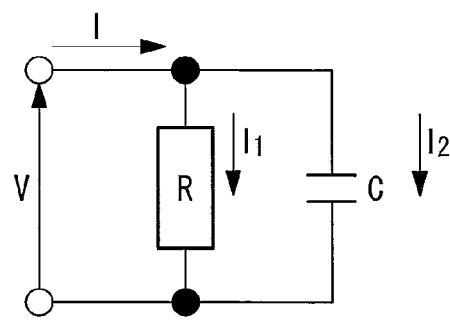
FIG. 2B is a circuit diagram of a circuit model.

First, as an equivalent electrical model of the plates 21 and 22 and the oil 20 lying between the plates 21 and 22 shown in FIG. 2A, a parallel circuit of a resistor R (R is the resistance value of the structure) and a capacitor C (the capacitance value of the oil lying between the plates) is assumed, as shown in FIG. 2B.

Let V be the voltage applied by the AC source 23, $\omega$ the frequency of the voltage V, I the flowing current, I1 the current flowing in the resistor R, and I2 the current flowing in the capacitor C; then the circuit equations are shown in the following expressions.

$$I = I1 + I2 \quad (1)$$

$$V = R \cdot I1 \quad (2)$$

$$V = (1/j\omega C) \cdot I2 \quad (3)$$

Therefore, from the expressions (1) to (3), the complex impedance Z of the parallel circuit is determined by the following expression:

$$Z = V/I = V/(((1/R) + j\omega C) \cdot V) = 1/((1/R) + j\omega C) \quad (4)$$

Figure 2C:
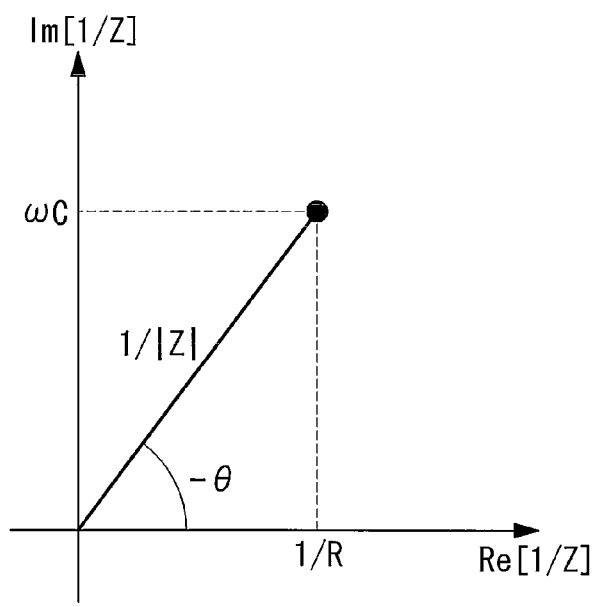
FIG. 2C is an explanatory diagram for explaining complex impedance Z in a complex plane.

Here, FIG. 2C shows the reciprocal 1/Z of the complex impedance Z, plotted on a complex plane. In this graph, the horizontal axis denotes the real part Re[1/Z] of the reciprocal 1/Z of the complex impedance Z, and the vertical axis denotes the imaginary part Im[1/Z] of the reciprocal 1/Z of the complex impedance Z. Furthermore, the linear distance from the center to a plotted point is the magnitude 1/|Z| of the reciprocal 1/Z of the complex impedance Z, and $\theta$ denotes the deflection angle of the reciprocal 1/Z of a complex impedance Z.

As shown in FIG. 2C, regarding the complex impedance Z obtained by measurement, since the real part of the reciprocal 1/Z thereof corresponds to the resistance component (1/R) and the imaginary part of the reciprocal 1/Z corresponds to the capacitance component ($\omega C$), the resistance value R and the capacitance value C can be determined. In addition, regarding the plates 21 and 22 and the oil 20 lying between the plates, since the distance d between the plates 21 and 22 and the area S of the planar surface are constant and predetermined, the electrical conductivity $\sigma$ and the dielectric constant $\in$ of the oil 10 can be determined based on the obtained resistance value R and the capacitance value C.

Figure 3:
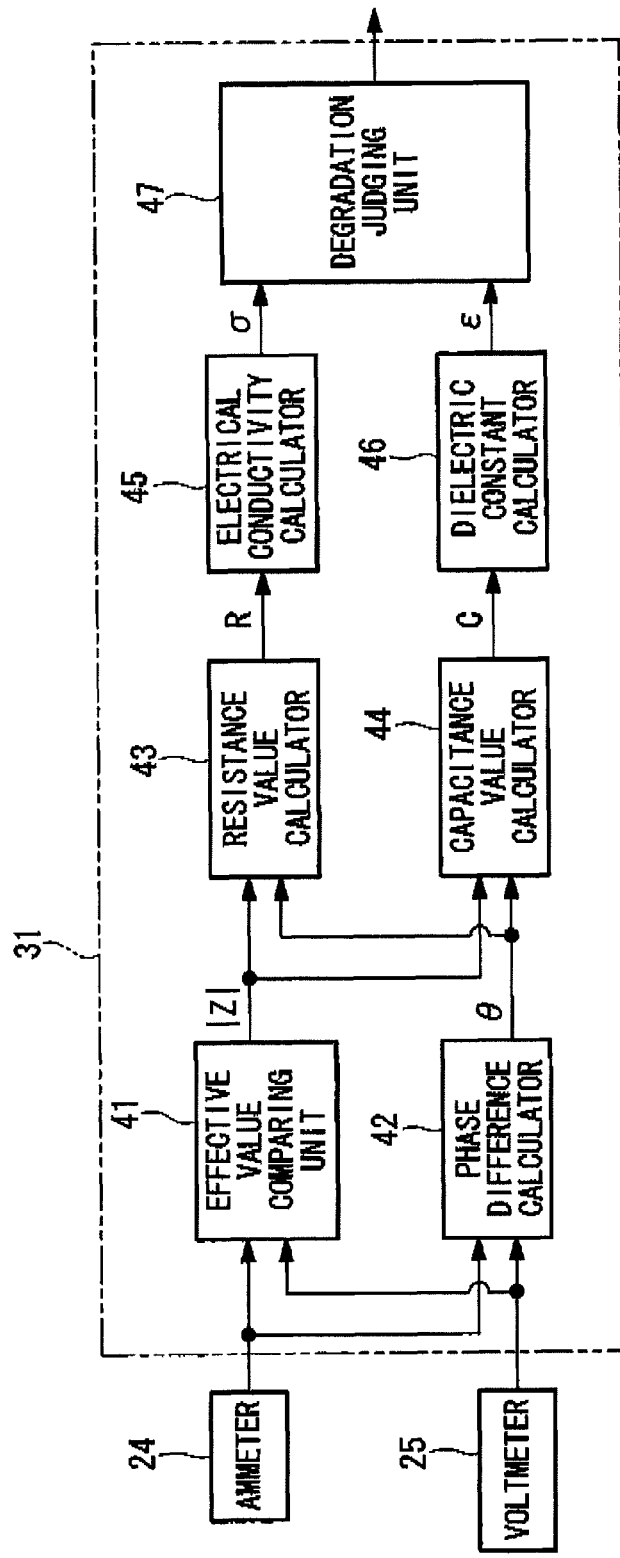
FIG. 3 is a detailed configuration diagram of a signal processor 31.

Next, signal processing and judgment processing in the signal processor 31 will be described in detail with reference to FIG. 3 showing a detailed configuration diagram of the signal processor 31. As shown in the diagram, the signal processor 31 is formed of an effective value comparing unit 41, a phase difference calculator 42, a resistance value calculator 43, a capacitance value calculator 44, an electrical conductivity calculator 45, a dielectric constant calculator 46, and a degradation judging unit 47. Furthermore, these components together represent the processing of the program. The ammeter 24 sends the effective value and phase of a current, and the voltmeter 25 sends the effective value and phase of a voltage.

First, the effective value comparing unit 41 determines the absolute value (|Z|=|V|/|I|) of the complex impedance Z by comparing the effective value of the current and the effective value of the voltage. The phase difference calculator 42 calculates the phase difference $\theta$ between the current and the voltage.

The resistance value calculator 43 determines the resistance value R (R=|Z|/cos $\theta$) from the reciprocal 1/|Z| of the complex impedance Z, and the capacitance value calculator 44 determines the capacitance value C (C=sin $\theta$/($\omega \cdot$|Z|)) from the reciprocal 1/|Z| of the complex impedance Z.

The electrical conductivity calculator 45 determines the electrical conductivity $\sigma$ ($\sigma$=d/R$\cdot$S) of the oil 10 from the resistance value R, and the dielectric constant calculator 46 determines the dielectric constant $\in$ ($\in$=C$\cdot$d/S) of the oil 10 from the capacitance value C.

In the degradation judging unit 47, for example, acceptable ranges from the upper limit to the lower limit of the respective electrical conductivity $\sigma$ and the dielectric constant $\in$ of the oil 10 are set in advance, and the oil is judged to be degraded when either the electrical conductivity $\sigma$ or the dielectric constant $\in$ is outside the respective acceptable range.

It is desirable to perform the measurement while varying the frequency of the AC voltage applied to the two plates. In general, when the frequency of the applied Ac voltage is relatively low, the change in signal due to the effect of a change in dielectric constant is decreased. Conversely, when the frequency is relatively high, the change in signal due to the effect of a change in dielectric constant tends to increase. That is, the sensitivities of the electrical conductivity $\sigma$ and the dielectric constant $\in$ can be controlled by making the frequency of the AC voltage variable.

For example, it is possible to confirm an AC voltage frequency band where higher sensitivities of the electrical conductivity $\sigma$ and the dielectric constant $\in$ are exhibited and degradation judgment can be performed more accurately according to the properties of oil 10 by performing measurement in a plurality of frequencies in preliminary experiment. During the operation of a system to which the oil-degradation detecting apparatus is applied, degradation of the oil 10 can be judged with higher precision by judging the degradation based on the electrical conductivity $\sigma$ and the dielectric constant $\in$ that are obtained by measuring at a plurality of frequencies and statistically processing them.

As described above, in the oil-degradation detecting apparatus of this Embodiment, the two plates 21 and 22 are disposed in the oil flow path 11 so as to be parallel to each other. A current that flows when an AC voltage applied between the two plates 21 and 22 is measured by the ammeter 24, and the voltage between the plates 21 and 22 is measured by the voltmeter 25. The signal processor (processor) 31 determines the electrical conductivity $\sigma$ and the dielectric constant $\in$ of the oil 10 based on the measurement results from the ammeter 24 and the voltmeter 25, and the degradation of the oil 10 is judged based on the electrical conductivity $\sigma$ and the dielectric constant $\in$.

Specifically, the ammeter 24 measures the instantaneous value of the current, and the voltmeter measures the instantaneous value of the voltage. The signal processor (processor) 31 determines the complex impedance Z between the plates 21 and 22 and the phase based on the measurement results from the ammeter 24 and the voltmeter 25. The electrical conductivity s of the oil 10 is determined by assuming the real part of the reciprocal of the complex impedance Z as the resistance component between the two plates 21 and 22, and the dielectric constant e of the oil is determined by assuming the imaginary part of the reciprocal of the complex impedance Z as the capacitance component between the two plates 21 and 22.

Figure 4:
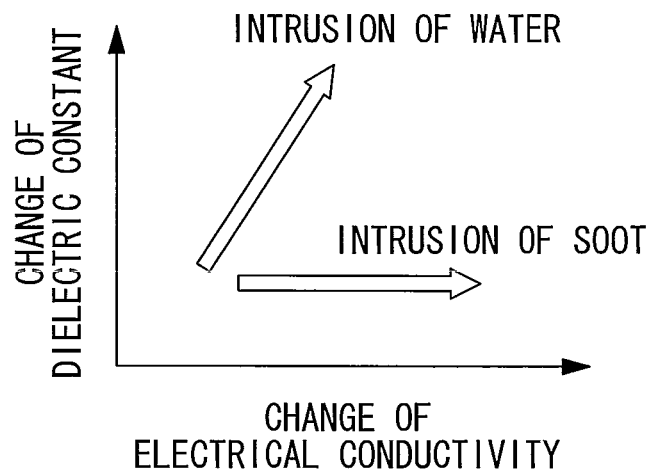
FIG. 4 is an explanatory diagram illustrating the tendency of changes in electrical conductivity and dielectric constant.

Changes in the electrical characteristics (electrical conductivity and dielectric constant) of the oil 10 are typically caused by intrusion of water, thermal degradation, or intrusion of soot. As shown in FIG. 4, the intrusion of water causes a large change in the dielectric constant, but the change in the electrical conductivity is relatively small. On the other hand, the intrusion of soot causes a large change in the electrical conductivity, but the dielectric constant is hardly changed. Therefore, as in a conventional case, degradation judgment of oil on the basis of a change in the electrical characteristics of only the electrical conductivity or the dielectric constant has limited accuracy. On the other hand, since the oil-degradation detecting apparatus of this Embodiment judges degradation of the oil 10 based on the electrical conductivity and the dielectric constant, electrical characteristics associated with degradation of the oil or intrusion of a contaminant can be ascertained two-dimensionally from the viewpoints of the electrical conductivity and the dielectric constant. In addition, degradation of oil caused by materials, such as soot, that highly affect the change in the electrical conductivity can be separately evaluated. As a result, oil degradation can be more accurately judged.

Figure 5:
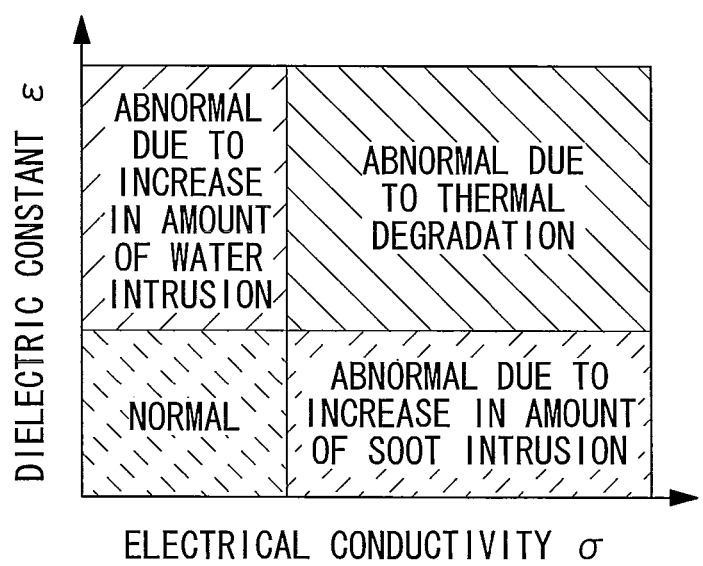
FIG. 5 is a diagram showing an example of a table stored by a degradation judging unit.

In this Embodiment, as shown in FIG. 5, for example, the degradation judging unit 47 includes a table that relates the electrical conductivity σ and the dielectric constant ∈ with causes of oil degradation. The cause of the oil degradation, in other words, the cause of the change of electrical characteristics (electrical conductivity and dielectric constant), may be identified by referring to this table.

Specifically, when both the electrical conductivity σ and the dielectric constant ∈ of the oil 10 are within the acceptable ranges, it is judged to be normal. When the electrical conductivity σ is outside the acceptable range and the dielectric constant ∈ is within the acceptable range, it is judged to be abnormal due to an increase in the amount of soot intrusion. When the electrical conductivity σ of the oil 10 is within the acceptable range and the dielectric constant ∈ of the oil 10 is outside the acceptable range, it is judged to be abnormal due to an increase in the amount of water intrusion. When both the electrical conductivity a and the dielectric constant ∈ of the oil 10 are outside the acceptable ranges, it is judged to be abnormal due to thermal degradation.

Furthermore, the measurement histories of the electrical conductivity σ and the dielectric constant ∈ of the oil 10 are periodically stored in a memory unit (not shown) in the signal processor 31 and may be used for judging the progress of degradation of the oil 10 and the time for an oil change.

Though the Embodiments of the present invention are described above with reference to the drawings, the specific configuration is not limited to these Embodiments: for example, design modifications that do not depart from the gist of the present invention are also included.

Modification 1

For example, a viscometer (viscosity sensor) for measuring the viscosity of the oil 10 may be further provided in the oil flow path 11, and the signal processor (processor) 31 may judge the degradation of the oil 10 by additionally using the measurement result from the viscometer (viscosity sensor).

In the above-described Embodiment, the degradation of the oil 10 is judged based on the electrical characteristics, i.e., the electrical conductivity and the dielectric constant ∈, of the oil 10, and there is difficulty in determining intrusion of a material (for example, fuel in the case where the oil-degradation detecting apparatus is applied to an internal-combustion engine) having similar electrical characteristics to those of the oil 10. Accordingly, as in Modification 1, it becomes possible to compensate for a decrease in the viscosity due to, for example, intrusion of fuel (judge degradation of the oil 10 and inform it) by adding viscosity to the judgment parameters of the degradation judgment of the oil 10. That is, the degradation of the oil 10 can be judged multidimensionally based on the electrical characteristics (electrical conductivity and dielectric constant) and the viscosity, and thereby the degradation judgment can be performed with higher precision and accuracy.

Modification 2

For example, a moisture meter for measuring the moisture of the oil 10 may be further provided in the oil flow path 11, and the signal processor (processor) 31 may judge the degradation of the oil 10 by additionally using the measurement result from the moisture meter.

Changes in the electrical characteristics (electrical conductivity and dielectric constant) of the oil 10 are typically caused by intrusion of water, thermal degradation, or intrusion of soot, but when a change in the electrical characteristics (electrical conductivity and dielectric constant) is small, there is difficulty in determining which is the cause. Accordingly, as in Modification 2, it becomes possible to determine which is the cause of the change in the electrical characteristics (electrical conductivity and dielectric constant) by adding moisture to the judgment parameters of the degradation judgment of the oil 10. That is, the degradation of the oil 10 can be judged multidimensionally based on the electrical characteristics (electrical conductivity and dielectric constant) and the moisture, and thereby the degradation judgment can be performed with higher precision and accuracy.

Modification 3

In addition, in the above-mentioned Embodiment, a sine wave is used as the waveform of the AC voltage, but a square wave, a triangle wave, a sawtooth wave, or a reverse sawtooth wave may be used. In such a case, harmonic components that are the integral multiple of the fundamental frequency can be obtained by Fourier transformation of the time function of the resulting impedance, and the electrical conductivities and the dielectric constants for a plurality of frequencies can be obtained simultaneously by determining the electrical conductivity and the dielectric constant of each harmonic component. That is, in the Embodiment, in order to increase the sensitivity, a plurality of frequencies is used as samples, and a more appropriate frequency is selected for measurement. However, information of a plurality of frequencies can be obtained by using a square wave, a triangle wave, a sawtooth wave, or a reverse sawtooth wave, and thereby a more accurate frequency index can be obtained by a single measurement. In addition, the resulting electrical conductivities σ and dielectric constants ∈ at a plurality of frequency points can be used for degradation judgment of the oil 10, and therefore it is possible to judge the degradation with higher precision.

Modification 4

It is also possible to use a configuration further provided with a partial changing unit that replaces part of the oil 10 with oil of good quality when the signal processor (processor) 31 judges that the oil 10 is degraded.

Figure 6:
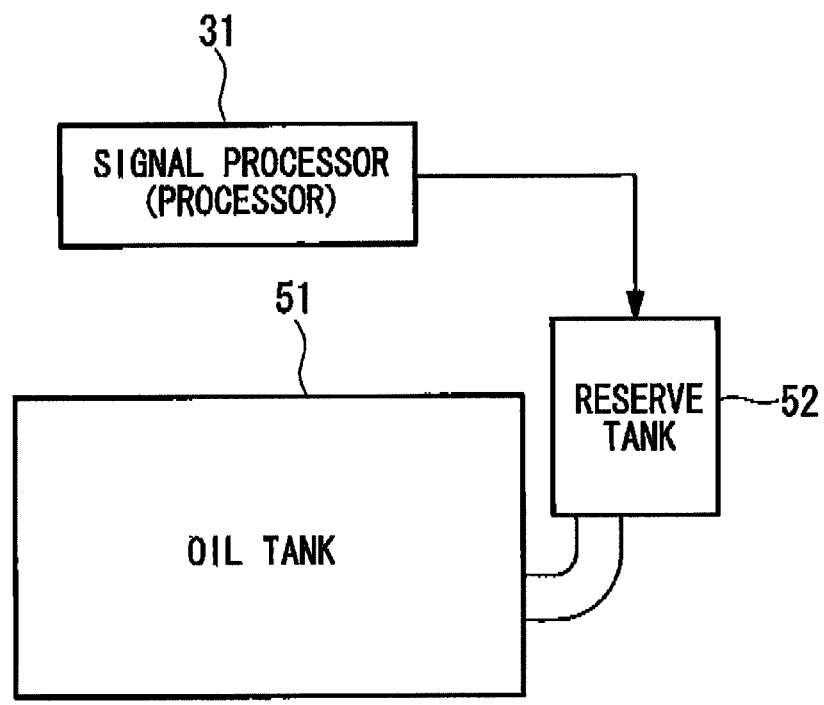
FIG. 6 is an explanatory diagram of a partial changing unit.

For example, as shown in FIG. 6, the apparatus is configured so that an oil tank 51 that supplies oil 10 to the oil flow path 11 includes a reserve tank 52 having a control valve, and the control valve is opened according to a control signal from the signal processor 31, when the signal processor 31 judges that the oil 10 is degraded, to replace part of the oil in the oil tank 51 with oil of good quality.

Thus, when the oil 10 is judged to be degraded by the signal processor 31, the informing unit 32 reports that fact, and at the same time, the oil 10 is partially changed. This gives some time until maintenance of the system to which the oil-degradation detecting apparatus is applied. In addition, it can prevent the worst case scenario, for example, breakage of the system, which may be caused by delayed maintenance.

Industrial Applicability

The oil-degradation detecting apparatus of the present invention can be applied to any mechanical system that circulates and supplies oil to the components of the system and thereby smoothly operates each component while preventing them from becoming worn. For example, the oil-degradation detecting apparatus can be applied to a mechanical system having a rotating part or a sliding part, specifically, various systems such as an internal-combustion engine using gasoline, diesel, or the like, a generator, an engine, or the rotating part of a wind, hydraulic, thermal, or nuclear power generator system.

By applying the oil-degradation detecting apparatus of the present invention to such a mechanical system, real-time sensing of oil degradation is possible without shutting down of the system. Furthermore, it is possible to determine the appropriate time for oil change, and thereby an advantage is afforded in that unnecessary oil change work can be avoided.

The invention claimed is:

1. An oil-degradation detecting apparatus comprising:
   two plates disposed so as to be parallel to each other in a path in which oil flows;
   an ammeter measuring the current that flows when an AC voltage is applied between the two plates;
   a voltmeter measuring the voltage between the plates when the AC voltage is applied to the two plates;
   a processor determining the electrical conductivity and the dielectric constant of the oil based on measurement results from the ammeter and the voltmeter and judging degradation of the oil based on the electrical conductivity and the dielectric constant;
   a viscometer disposed in the oil flow path measuring viscosity of the oil; and
   a moisture meter disposed in the oil flow path measuring moisture in the oil, wherein
   the processor judges degradation of the oil by additionally using a measurement result from the viscometer and a measurement result from the moisture meter with the electrical conductivity and the dielectric constant of the oil,
   the processor judges that the condition of the oil is normal when the electrical conductivity of the oil and the dielectric constant of the oil are within predetermined acceptable ranges,
   the processor judges that the condition of the oil is abnormal due to an increase in an amount of soot intrusion when the electrical conductivity of the oil is outside the acceptable range and the dielectric constant of the oil is within the acceptable ranges,
   the processor judges that the condition of the oil is abnormal due to an increase in an amount of water intrusion when the electrical conductivity of the oil is within the acceptable range and the dielectric constant of the oil is outside the acceptable ranges, and
   the processor judges that the condition of the oil is abnormal due to thermal degradation when both the electrical conductivity of the oil and the dielectric constant of the oil are outside the acceptable ranges.

2. The oil-degradation detecting apparatus according to claim 1, wherein
   the ammeter measures a current;
   the voltmeter measures a voltage; and
   the processor determines the complex impedance between the two plates and the phase difference between the current and the voltage based on the measurement results from the ammeter and the voltmeter, determines the electrical conductivity of the oil by assuming the real part of the reciprocal of the complex impedance as the resistance component between the two plates, and determines the dielectric constant of the oil by assuming the imaginary part of the reciprocal of the complex impedance as the capacitance component between the two plates.

3. The oil-degradation detecting apparatus according to claim 1, further comprising:
   an informing unit reporting the result of the judgment of degradation of the oil by the processor.

4. The oil-degradation detecting apparatus according to claim 1, further comprising:
   a partial changing unit that replaces part of the oil with oil of good quality when the processor judges the oil to be degraded.

5. The oil-degradation detecting apparatus according to claim 1, wherein the measurement is performed while varying the frequency of the AC voltage applied to the two plates.

6. The oil-degradation detecting apparatus according to claim 1, wherein the waveform of the AC voltage applied to the two plates is a sine wave, a square wave, a triangle wave, a sawtooth wave, or a reverse sawtooth wave.

7. A mechanical system including a rotating part or a sliding part, comprising the oil-degradation detecting apparatus according to claim 1.

* * * * *